(12) United States Patent
Carron et al.

(10) Patent No.: US 9,730,766 B2
(45) Date of Patent: *Aug. 15, 2017

(54) PROPHY ANGLE AND ADAPTER WITH GUARD

(71) Applicant: Avid Incorporated, Bloomsdale, MO (US)

(72) Inventors: Chris J. Carron, Bloomsdale, MO (US); David G. Grither, Ste. Genevieve, MO (US)

(73) Assignee: Avid Incorporated, Bloomsdale, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/837,367

(22) Filed: Aug. 27, 2015

(65) Prior Publication Data

US 2015/0359606 A1    Dec. 17, 2015

Related U.S. Application Data

(63) Continuation of application No. 12/713,088, filed on Feb. 25, 2010, now Pat. No. 9,144,471, which is a
(Continued)

(51) Int. Cl.
*A61C 1/12*        (2006.01)
*A61C 1/14*        (2006.01)
(Continued)

(52) U.S. Cl.
CPC ............... *A61C 1/141* (2013.01); *A61C 1/05* (2013.01); *A61C 1/12* (2013.01); *A61C 17/005* (2013.01); *A61C 1/185* (2013.01)

(58) Field of Classification Search
CPC .. A61C 1/12; A61C 1/141; A61C 1/05; A61C 17/005; A61C 1/185; A61C 1/188
(Continued)

(56) References Cited

U.S. PATENT DOCUMENTS 1,170,524 A * 2/1916 Fernald .................... A61C 1/12
                                                   433/130
1,688,136 A * 10/1928 Chayes ................. A61C 1/141
                                                   279/76
(Continued)

FOREIGN PATENT DOCUMENTS

FR                 75885 E * 8/1961 ............... A61C 1/12

*Primary Examiner* — Tatiana Nobrega
(74) *Attorney, Agent, or Firm* — CRGO Law; Steven M. Greenberg, Esq.; Kara A. Brotman, Esq.

(57) ABSTRACT

A dental system comprises a dental prophy angle and an adjustable angle adapter. The prophy angle includes a housing and a guard with a concave inner surface. The adapter is configured to drive the prophy angle and the adapter includes a body, a nose, and an outer joint. The nose is configured to receive a portion of a prophy angle. The body is adjustably connected to the nose. The outer joint includes a ball portion connected to the nose, and a ball receiver positioned on the body. The ball receiver includes a first portion coupled to a first end of the body and a second portion attachable to the first portion. The nose is rotatable relative to the body into at least a first configuration and a second configuration. The concave inner surface of the guard engages a convex outer surface of the ball receiver.

10 Claims, 14 Drawing Sheets

Related U.S. Application Data continuation-in-part of application No. 12/503,151, filed on Jul. 15, 2009, now abandoned, which is a continuation-in-part of application No. 11/862,628, filed on Sep. 27, 2007, now Pat. No. 8,123,523, which is a continuation-in-part of application No. 11/682,927, filed on Mar. 7, 2007, now abandoned, which is a continuation-in-part of application No. 11/189,193, filed on Jul. 26, 2005, now Pat. No. 7,422,433.

(51) Int. Cl.
    *A61C 1/05*   (2006.01)
    *A61C 17/00*  (2006.01)
    *A61C 1/18*   (2006.01)

(58) Field of Classification Search
    USPC ........ 433/103, 112, 114, 115, 116, 124, 125, 433/126, 130, 133, 118; 606/78–83, 167; 464/171, 173; 81/57.13, 57.29
    See application file for complete search history.

(56) References Cited

U.S. PATENT DOCUMENTS

| | | | | |
|---|---|---|---|---|
| 4,281,989 | A | * | 8/1981 | Glover ................... A61C 1/12 433/115 |
| 5,433,605 | A | * | 7/1995 | Strobl, Jr. ............ A61C 17/005 433/112 |
| 7,422,433 | B2 | | 9/2008 | Carron |
| 8,123,523 | B2 | | 2/2012 | Carron |
| 8,459,992 | B2 | | 6/2013 | Carron |
| 8,834,159 | B2 | | 9/2014 | Carron |
| 2008/0220392 | A1 | | 9/2008 | Carron |
| 2010/0015568 | A1 | | 1/2010 | Carron |
| 2010/0196845 | A1 | | 8/2010 | Carron |

* cited by examiner

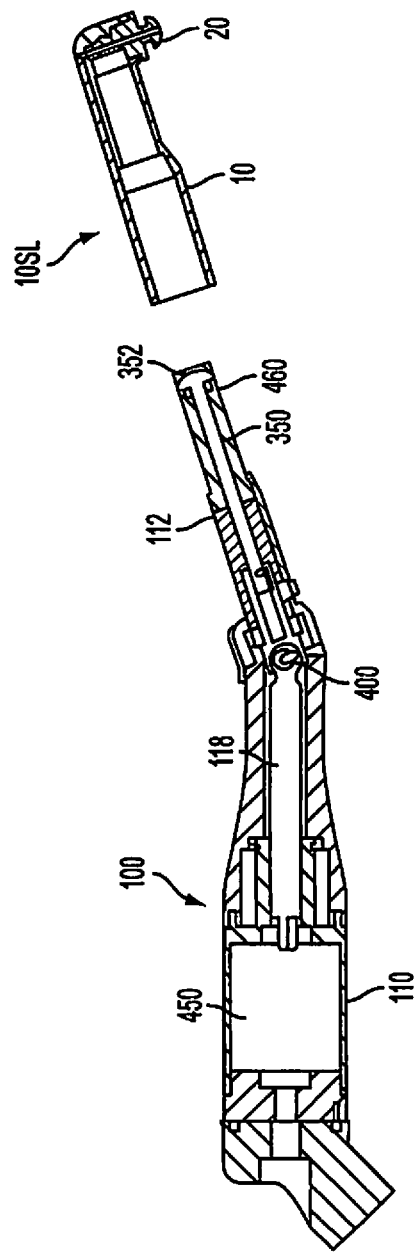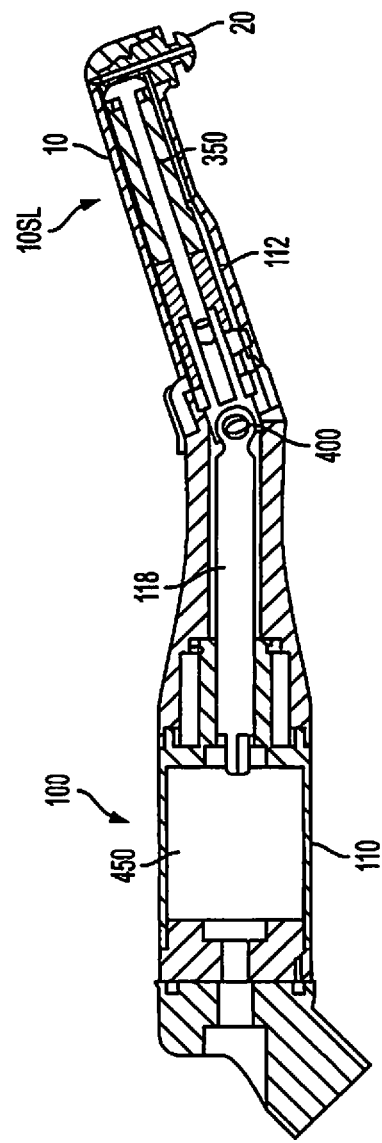
FIG. 19A
FIG. 19B

PROPHY ANGLE AND ADAPTER WITH GUARD

CROSS-REFERENCE TO RELATED APPLICATIONS

This application is a Continuation of U.S. patent application Ser. No. 12/713,088, filed Feb. 25, 2010, now U.S. Pat. No. 9,144,471, which is a Continuation-In-Part of U.S. patent application Ser. No. 12/503,151, filed on Jul. 15, 2009, now abandoned, which is a Continuation-In-Part of U.S. patent application Ser. No. 11/862,628, filed on Sep. 27, 2007, now U.S. Pat. No. 8,123,523, which is a Continuation-In-Part of U.S. patent application Ser. No. 11/682,927, filed on Mar. 7, 2007, now abandoned, which is a Continuation-In-Part of U.S. patent application Ser. No. 11/189,193, filed on Jul. 26, 2005, now U.S. Pat. No. 7,422,433, all of which are incorporated herein by reference in their entirety. This application is related to U.S. patent application Ser. No. 12/712,993, filed on Feb. 25, 2010, now U.S. Pat. No. 8,834,159, entitled "ADJUSTABLE ANGLE PROPHY ANGLE ADAPTER," and U.S. patent application Ser. No. 12/713,070, filed on Feb. 25, 2010, now U.S. Pat. No. 8,459,992, entitled "PROPHY ANGLE AND ADAPTER WITH LATCH," all of which are incorporated herein by reference in their entirety.

BACKGROUND OF THE INVENTION

Field of the Invention

The disclosure relates generally to dental instruments and, more specifically, to prophy angles and adapters for use with prophy angles.

Description of the Related Art

Dental prophylaxis angles, generally referred to as "prophy angles," are commonly used dental instruments for providing rotation for dental tools such as brushes, prophy cups, or other receptacles used in cleaning/polishing teeth. Referring to FIGS. 17 and 18, a prophy angle 10 typically includes a housing 16 having a neck 18 and a head portion 14 extending at approximately a 90° angle to the neck 18, which increases the ability of a dentist to reach various surfaces of the teeth of a patient. A drive shaft or prophy rotating member 12 can be located within the housing 16 and attached to a driven gear 20 in the head of the prophy angle. Prophy angles 10 are generally affixed to an adapter or hand piece (not shown), which connects the prophy angle to a drive source (not shown), thereby enabling a rotating motion of the prophy rotating member 12 and driven gear 20 of the prophy angle and any affixed dental tool.

Prophy angles 10 are commonly manufactured from lightweight plastic to make them disposable, thereby increasing overall sterility in the dental environment. An issue associated with making the prophy angles 10, and their constituent elements, such as the prophy rotating member 12, from plastic is the ability of the hand piece to engage the prophy rotating member 12 without slipping and to engage the prophy rotating member 12 without excessive damage to the prophy rotating member 12. Another issue associated with the use of prophy angles 10 is the widespread use of many different and incompatible types of couplings between the drive source and the hand piece and between the hand piece and the prophy angle 10. Yet another issue associated with the use of prophy angles 10 is the number of adapters needed to provide different orientations.

BRIEF SUMMARY OF THE INVENTION

A dental system comprises a dental prophy angle and an adjustable angle adapter. The prophy angle includes a housing and a guard with an inner surface of the guard being concave. The adapter is configured to drive the prophy angle and the adapter includes a body, a nose, and an outer joint. The nose is configured to receive a portion of a prophy angle. The body is adjustably connected to the nose. The outer joint includes a ball portion connected to the nose and a ball receiver positioned on the body. The ball receiver comprises a first portion and a second portion, the first portion is coupled to a first end of the body and the second portion is attachable to the first portion. The nose is rotatable relative to the body into at least a first configuration and a second configuration. The concave inner surface of the guard engages a convex outer surface of the ball receiver.

In certain aspects, the guard has a greatest outer diameter 10% larger than a greatest outer diameter of the housing, and in other aspects, the guard has a greatest outer diameter 20% larger than a greatest outer diameter of the housing.

In additional aspects, in the first configuration, the shaft and the rotating member share a common rotational axis. In the second configuration, a rotational axis of the shaft is at a non-zero degree angle to a rotational axis of the rotating member. The nose is rotatable relative to the body from between zero degrees to about twenty degrees. The guard includes an inner surface having a spherical radius that substantially matches a spherical radius of an outer surface of the ball receiver. The inner surface of the guard includes a plurality of inwardly-extending ribs. A seal is formed between the inner surface of the guard and the outer surface of the ball receiver. Also, a motor integral with the body can be provided.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIGS. 19A and 19B are, respectively, exploded and assembled cross-sectional views of a shaft-less prophy angle and adapter.

DETAILED DESCRIPTION OF THE INVENTION

Figure 1A:
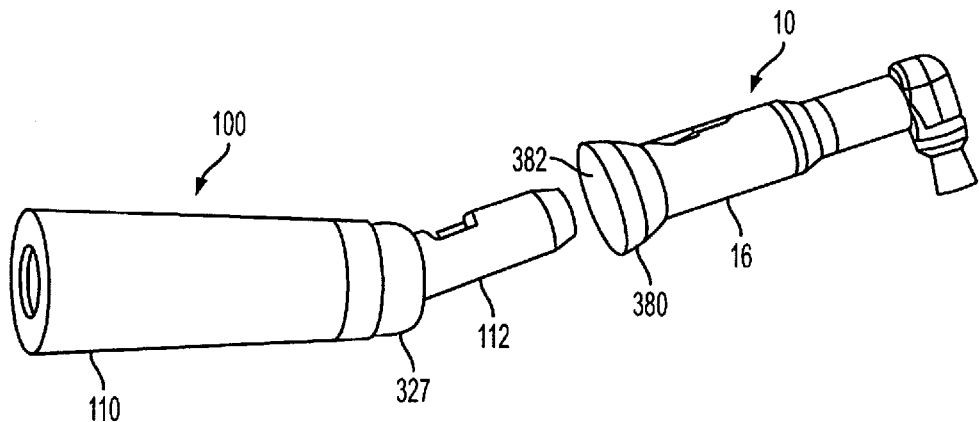
FIGS. 1A, 1B, and 1C are perspective views of a prophy angle with an integrated guard detached and attached to an adjustable angle adapter, in accordance with the inventive arrangements.
Figure 1B:
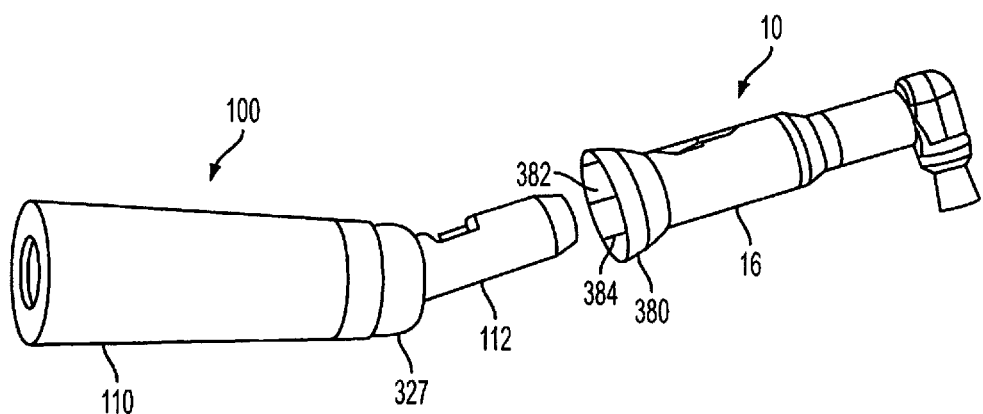
Figure 1C:
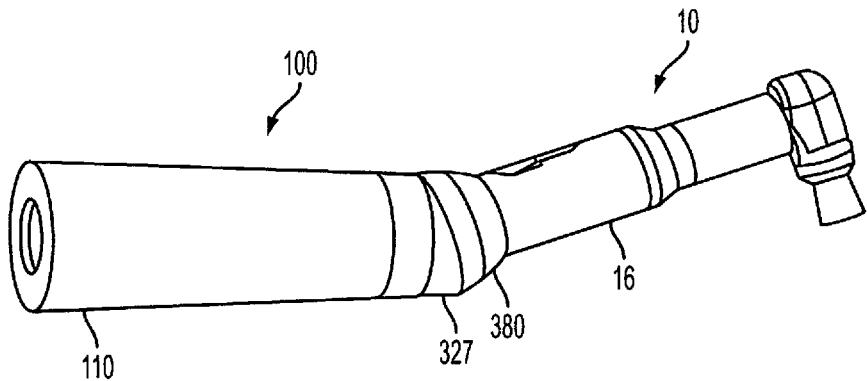

Referring to FIGS. 1A-1C, the guard 380 may be integrated into the housing 16 of the prophy angle 10. Further, an inner surface 382 of the guard 380 can be concave. In this way, the guard 380 can mate with the convex outer surface 327 of the ball receiver of the adapter 100. The adapter 100 can further include a body 110 and a nose 112. Since common practice is to treat the prophy angle 10 as a disposable item that is replaced each time the adapter 100 is used with a new patient, the guard 380 can also be replaced each time the prophy angle 10 is replaced. Since the guard 380 acts as a seal between the nose 112 and the ball receiver, each instance the prophy angle 10 is replaced, a new seal is provided between the nose 112 and the ball receiver.

As illustrated, the guard 380 extends from a receiving end of the housing 16. Additionally, the guard 380 has a greatest outer diameter is larger than a greatest outer diameter of the housing 16. Further, the inner surface 382 of the guard 380 may include a plurality of inwardly-extending ribs 384, as illustrated in FIG. 1B, or the inner surface 382 of the guard 380 may be smooth, i.e. not including ribs, as shown in FIG. 1A. In certain aspects, the greatest outer diameter of the guard 380 is 10% greater than the greatest outer diameter larger than a greatest outer diameter of the housing 16. In other aspects, the greatest outer diameter of the guard 380 is 20% greater than the greatest outer diameter larger than a greatest outer diameter of the housing 16.

Figure 2:
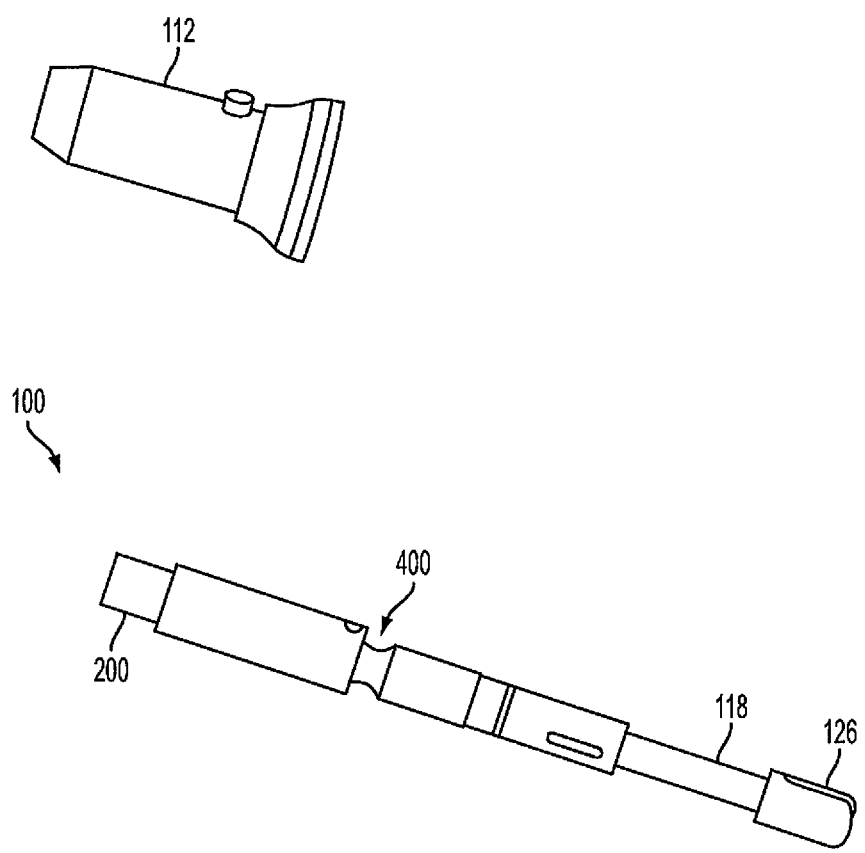
FIG. 2 is an exploded, side view of an adjustable angle adapter, in accordance with the inventive arrangement.

FIG. 2 illustrates an exemplar adjustable angle adapter 100 for use with a prophy angle. The adapter 100 includes a body and a nose 112. The adapter 100 includes a shaft 118, which is adjustably connected to a nose rotating member, such as a collet 200, for receiving a prophy rotating member of the prophy angle. The nose 112 includes a first bore for receiving the prophy rotating member and, in certain configurations, a portion of the shaft 118 and/or collet 200. In certain aspects, the adapter 100 includes a multi-axis rotation joint 400 that connects the shaft 118 to the nose rotating member (e.g., collet 200). Additionally, the adapter 100 includes an outer joint that connects the body to the nose 112.

As is known in the art, many different types of drive sources exist and these different drive sources have different configurations for coupling with a rotating member, such as the shaft 118. In this regard, the present adapter 100 is not limited as to the type and configuration of coupler 126 that couples with the drive source. However, in certain aspects of the adapter 100, the coupler 126 is an E-type coupler. Other types of couplers/connection devices have been previously described with regard to the nose 112.

The shaft 118 is rotated by the drive source, which is connected to a coupler 126 positioned on one end of the shaft 118, which drives a collet 200 connected on another end of the shaft 118. In certain configurations of the adjustable angle adapter 100, both the coupler 126 and the collet 200 rotate about a common rotational axis, RA. However, in other configurations of the adjustable angle adapter 100, the coupler 126 and the collet 200 rotate about different rotational axes, $RA_1$, $RA_2$.

Many types of shafts 118 are capable of transmitting rotation from the coupler 126 to the collet 200, and the present adjustable angle adapter 100 is not limited as to a particular type of shaft 118 so capable. As the rotational axis $RA_2$ of the shaft 118 may be at an angle to the rotational axis $RA_1$ of the collet 200, a multi-axis rotation joint (see discussion with regard to FIGS. 14A-14C and 15A-15B) is positioned between the collet 200 and the shaft 118 to transfer the rotation of the shaft 118 to the collet 200.

Figure 3:
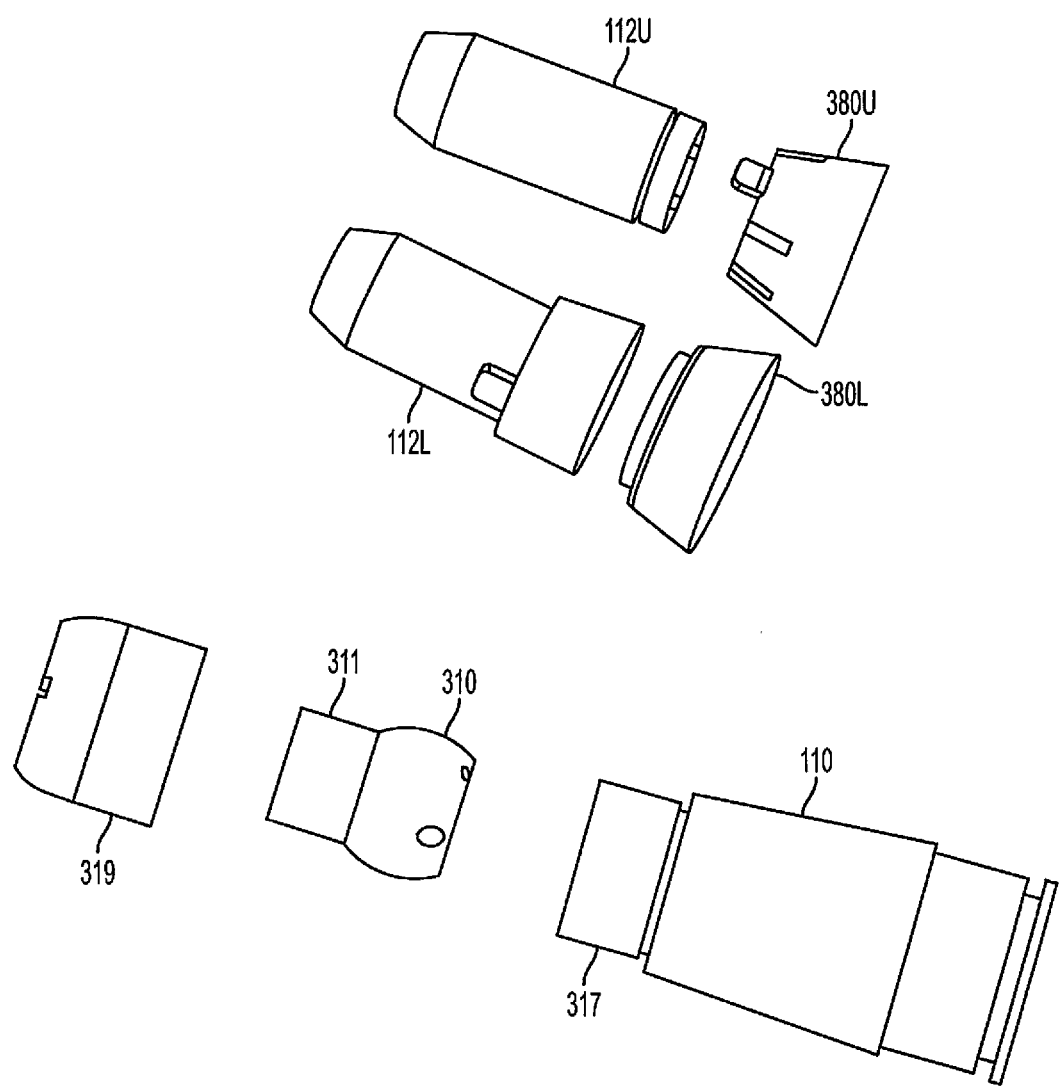
FIG. 3 is an exploded, side view of an adjustable angle adapter, in accordance with another embodiment of the inventive arrangement.

Referring specifically to FIG. 3, the nose and guard can have different configurations relative to one another. For example, in the upper configuration illustrated in FIG. 3, the nose 112U is inserted fully into the guard 380U and subsequently mates with a neck 311 of a ball portion 310. In the lower configuration, the nose 112L mates with a perpendicular face of the guard 380L. As can be readily envisaged, other configurations are possible. Although not limited in this manner, the assembly of an adapter 100 can include splitting the ball receiver 312 into two separate portions 317, 319, as illustrated in the bottom of FIG. 3 and, in part, in FIGS. 5 and 6.

Figure 5:
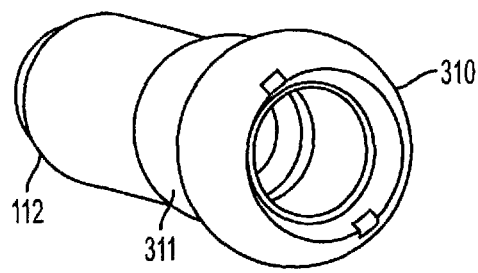
FIG. 5 is a perspective view of a ball portion and nose of the adjustable angle adapter, in accordance with the inventive arrangement.
Figure 6:
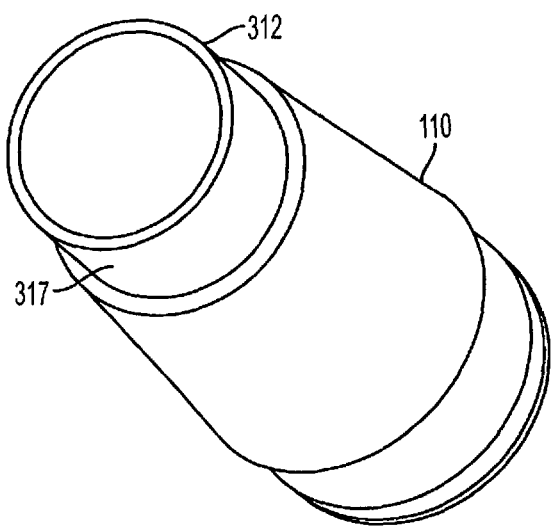
FIG. 6 is a perspective view of a ball receiver and body of the adjustable angle adapter, in accordance with the inventive arrangement.

As shown in the bottom portion of FIG. 3 and FIGS. 5 and 6, the first portion 317 is connected to the body 110 and the first portion 317 is attachable to the second portion 319 using, for example, mating threads. While the first portion 317 of the ball receiver 312 is separate from the second portion 319 of the ball receiver 312, the ball portion 310 having a neck 311 is inserted into the cavity defined by the inner surface of the ball receiver 312. The second portion 319 of the ball receiver 312 is then slid over the ball portion 310 and attached to the first portion 317 of the ball receiver 312. In so doing, the body 110 is joined to the nose 112 at an outer joint.

Figure 8:
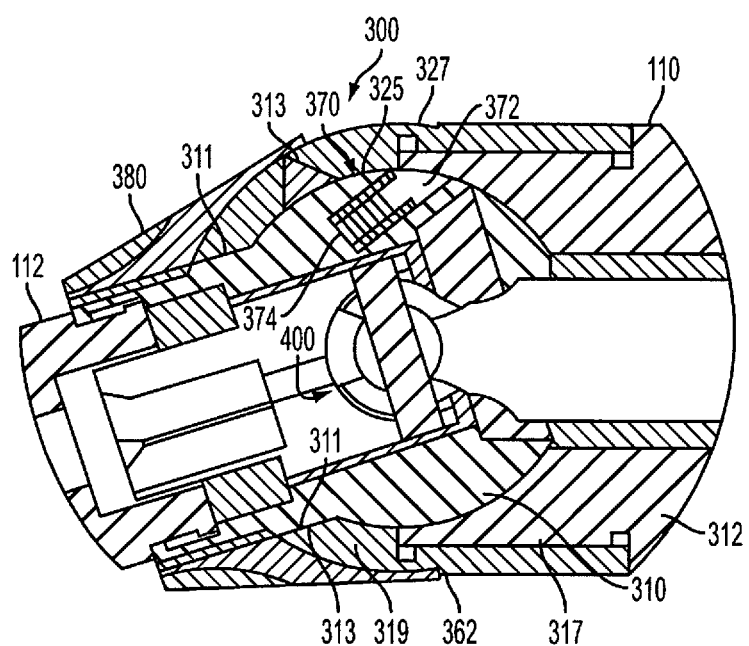
FIG. 8 is a detail, side cross-sectional view of an outer joint of the adjustable angle adapter, in accordance with the inventive arrangement.
Figure 14A:
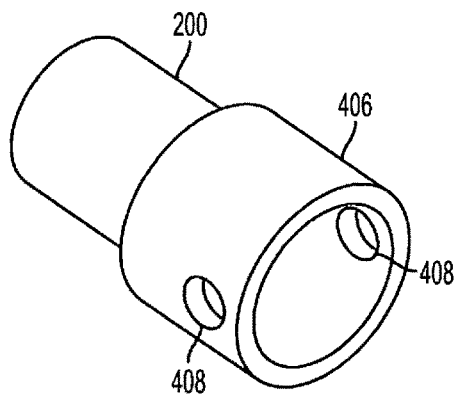
FIGS. 14A-14D are, respectively, a perspective view of a receiver, a perspective view of the receiver and a second pin, a perspective view of a first pin and the second pin, and a perspective view of the first pin and the second pin position within a head of a yoke and pin joint in accordance with the inventive arrangements.

It is further noted that multiple, different spherical surfaces between the dental prophy angle and the adapter share a common center point. For example, the following all share a common center point with each other: a convex spherical outer surface of a ball portion 310 that can mate with a concave spherical inner surface of a ball receiver 312, as illustrated in FIGS. 5 and 6; as seen in FIG. 8, a spherical convex outer surface 327 of the ball receiver 312, which can mate with the spherical concave inner surface of a guard 380; and, a convex spherical outer surface of a multi-axis rotation joint 400 can mate with the concave spherical inner surface of a receiver 406 that is connected to a collet 200, as shown in FIGS. 14A and 14D. It is further noted that there are additional spherical surfaces on non-rotating elements that share a common center point with the surfaces referenced above. For instance, there are two spherical surfaces that are associated with the drive mechanism that rotate on both RA1 and RA2 that share a common center point with the spherical surfaces referenced above.

Figures 4A, 4B:
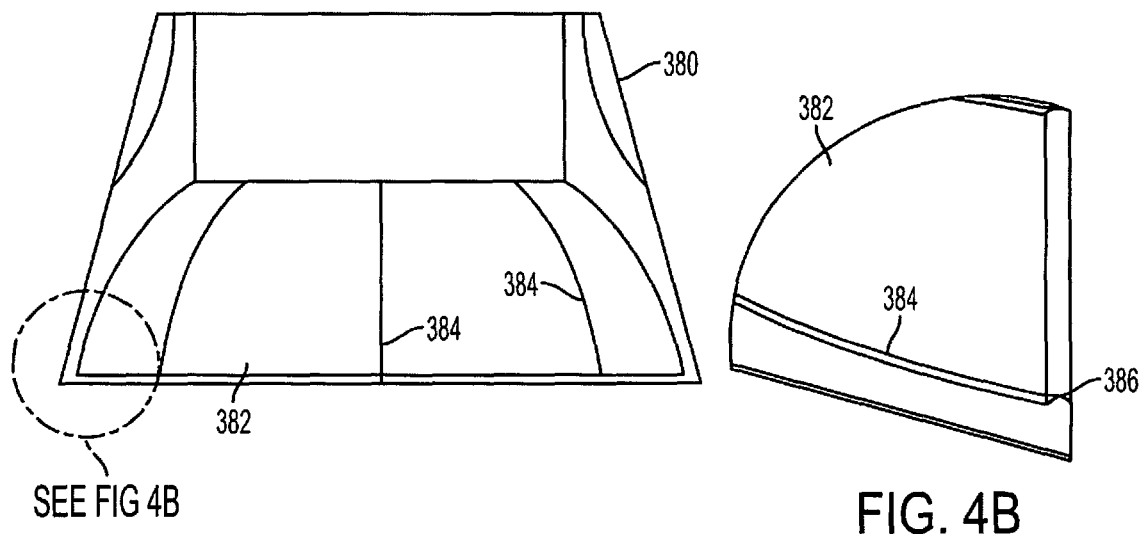
FIGS. 4A and 4B are, respective, a side and detail view of a guard, in accordance with the inventive arrangement.

In reference to FIGS. 4A and 4B, a guard 380 can be provided that creates a seal between the nose and the ball receiver. The guard 380 includes an inner surface 382 having a radius that substantially matches a radius of the outer surface of the ball receiver. Additionally, the guard 380 can include a sealing element 386 that engages the outer surface of the ball receiver to form a seal. This seal acts to prevent debris, during operation of the adapter, from entering the outer joint. As the nose pivots relative to the body, the sealing element 386 remains substantially in contact with the outer surface of the ball receiver to maintain the seal between the nose and the ball receiver.

By their very nature, seals tend to wear over time and/or use and become less effective. In certain aspects of the outer joint, the guard 380 can be considered a replaceable portion of the adapter 100. Also, although not limited in this manner, the guard 380 can be formed from an easily-fashioned material, such as autoclavable plastic. The outer joint is not limited in the manner in which the guard 380 can be replaceable. For example, referring to FIG. 3, the guard 380U, 380L may be removably attachable to the nose 112U, 112L, and the manner by which the guard 380U, 380L is removably attachable to the nose 112U, 112L is not limited. For example, the guard 380U, 380L may screw onto the nose 112U, 112L. Alternatively, one or more removable pins may be used to attach the guard 380U, 380L to the nose 112U, 112L. Additionally, the guard 380U may screw onto the neck 311 of the ball portion 310. In certain aspects, the guard 380L floats between the nose 112L and the ball receiver 327.

In addition, the inner surface 382 of the guard 380 may include a plurality of inwardly-extending ribs 384 to engage the outer surface of the ball receiver. The ribs 384 provide a grabbing surface with which the guard 380 can prevent movement of the guard 380 relative to the ball receiver upon outside pressure being placed against the guard 380, thereby preventing movement of the body relative to the nose. Although the ribs 384 are illustrated as being disposed on the guard 380, the ribs 384 may be disposed on the outer surface of the ball receiver. Additionally, although the ribs 384 are illustrated as radiating from a center, the ribs 384 may be configured to constitute a plurality of concentric circles. In a different embodiment, the inner surface 382 of the guard 380 may be smooth, i.e. include no ribs (see FIG. 1A).

Figure 7A:
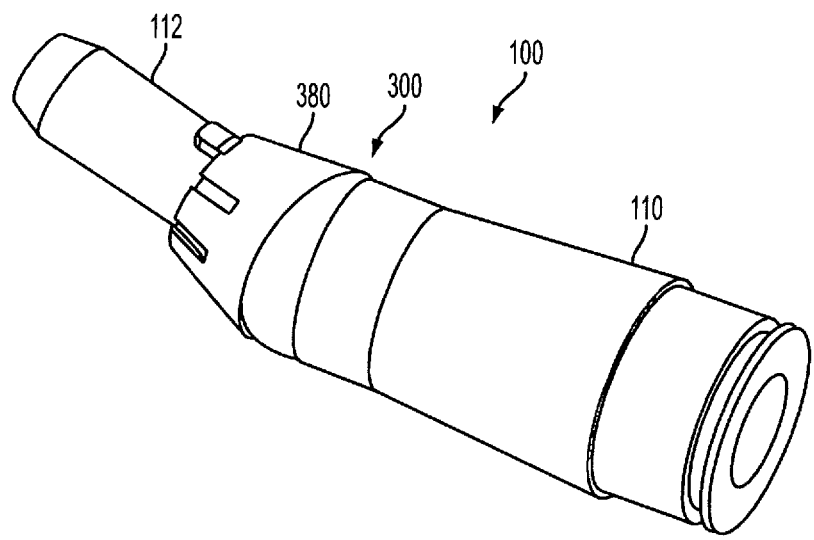
FIGS. 7A and 7B are perspective views of the adjustable angle adapter, respectively, in contra-style and straight orientations.
Figure 7B:
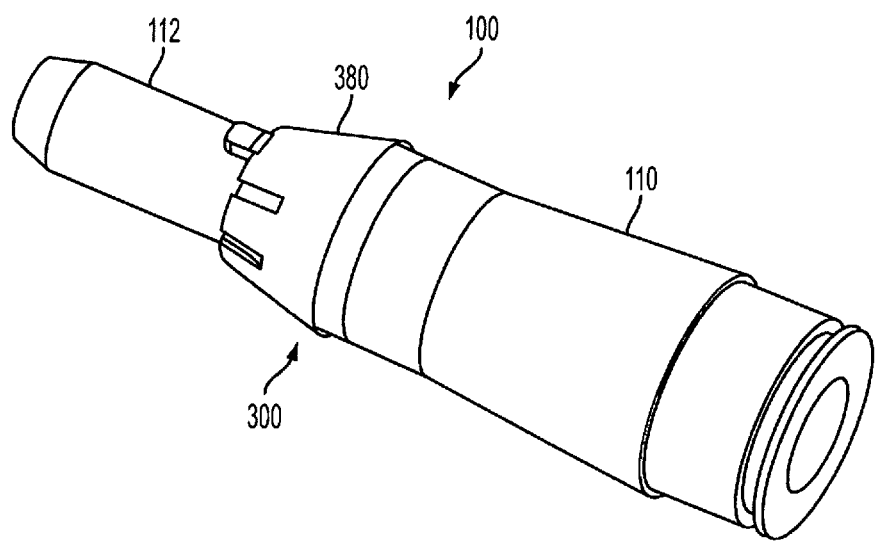

Referring to FIGS. 7A and 7B, an embodiment of an outer joint 300 for an adapter 100 is illustrated. In this particular embodiment, the ball receiver is positioned on the body 110, and the ball portion is positioned on the nose 112. In addition, a guard 380 is coupled to the nose 112. This embodiment of the outer joint 300 can also include a stop that defines a maximum angle that the body 110 can pivot relative to the nose 112.

In further illustration of an adjustable angle adapter with a multi-axis rotation joint 400 and an outer joint 300, FIG. 8 shows a portion of the nose 112 (e.g., the neck 311 of ball portion 310) will ultimately engage a portion of the body 110 (e.g., an angled surface 313 of the ball receiver 312 that extends from the inner surface 325 to the outer surface 327 of the ball receiver 312). Additionally, by angling the surface 313, as opposed to having a face that is perpendicular to the inner surface 325 of the ball receiver 312 or the outer surface 327 of the ball receiver 312, a greater proportion of outer surface 327 of the ball receiver 312 can be any contact with an inner surface of a guard 380 at any given angular configuration. In this configuration, upon the nose 112 engaging the body 110, a maximum angle that the body 110 can pivot relative to the nose 112 can be defined. Additional and/or alternative configurations can also be used to define the maximum angle that the body 110 can pivot relative to the nose 112. In one embodiment, at a particular angle of the body 110 relative to the nose 112, the distal end of the guard 380 may engage a shoulder 362 in the outer surface 327 of the ball receiver 312. In this manner, the maximum angle that the body 110 can pivot relative to the nose 112 can be defined. Further, although not limited in this manner, in certain aspects of the adapter, the multi axis rotation joint 400 and the outer joint 300 pivot about a common pivot point.

Although not limited in this manner, FIG. 8 further illustrates that the ball receiver 312 can be split into two separate portions 317, 319. The first portion 317 is connected to the body 110 and the second portion is attachable to the second portion 319 using, for example, mating threads. While the second portion 319 of the ball receiver 312 is separate from the first portion 317 of the ball receiver 312, the ball portion 310 is inserted into the cavity defined by the inner surface 325 of the ball receiver 312. The second portion 319 of the ball receiver 312 is then slid over the ball portion 310 and attached to the first portion 317 of the ball receiver 312. In so doing, the body 110 is joined to the nose 112 at the outer joint 300.

FIG. 8 further indicates that in certain aspects of an adapter, one or more drag devices 370 may be included within the outer joint 300, the drag devices 370 act to increase the drag between the ball portion 310 and ball receiver 312 as the nose 112 pivots relative to the body 110. By increasing the drag between the ball portion 310 and the ball receiver 312, the nose 112 is less likely to pivot relative to the body 110 during use of the adapter and after the adjustment of the angle between the body 110 and the nose 112. Additionally, although the drag device 370 is illustrated with respect to the additional embodiment, the adapter is not limited in this manner, and the drag device 370 can be employed in the previous embodiment.

Although a single drag device 370 is illustrated, more than a single drag device 370 can be employed. Also, if more than a single drag device 370 is employed, these drag devices can be positioned equidistant to one another. In certain aspects of the outer joint 300, three drag devices 370 are provided and positioned 120 degrees apart.

Any type of drag device 370 capable of increasing the drag between the ball portion 310 and the ball receiver 312 as the nose 112 pivots relative to the body 110 is acceptable for use in the joint 300. However, in certain aspects, the drag device 370 includes a plunger 372 and a biasing means (e.g., a spring 374) positioned within a channel of either the ball receiver 312 or the ball portion 310. As illustrated, the drag device 370 is positioned within the ball portion 310. In certain aspects of the drag device 370, the outer surface of the plunger 372 substantially matches the outer radius of the ball portion 310.

Figure 9A:
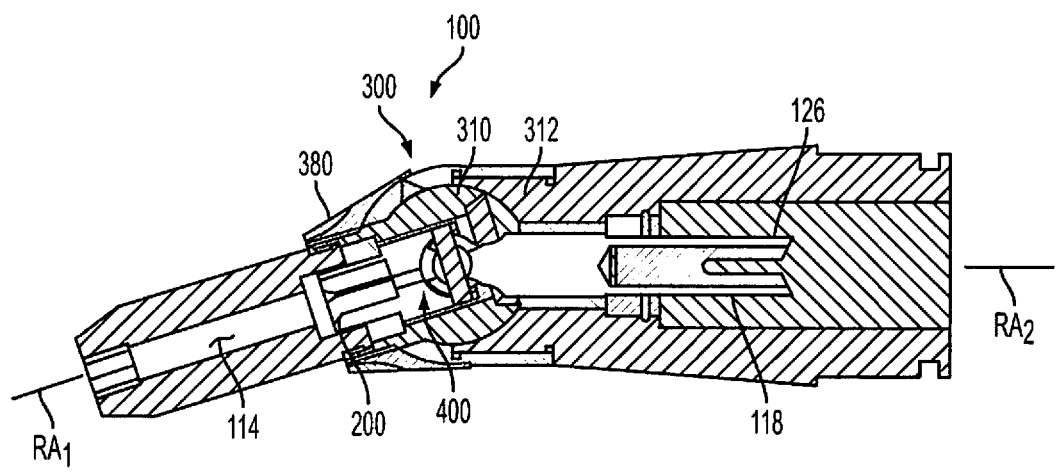
FIGS. 9A and 9B are side cross-sectional views of the adjustable angle adapter, respectively, in contra-style and straight orientations.
Figure 9B:
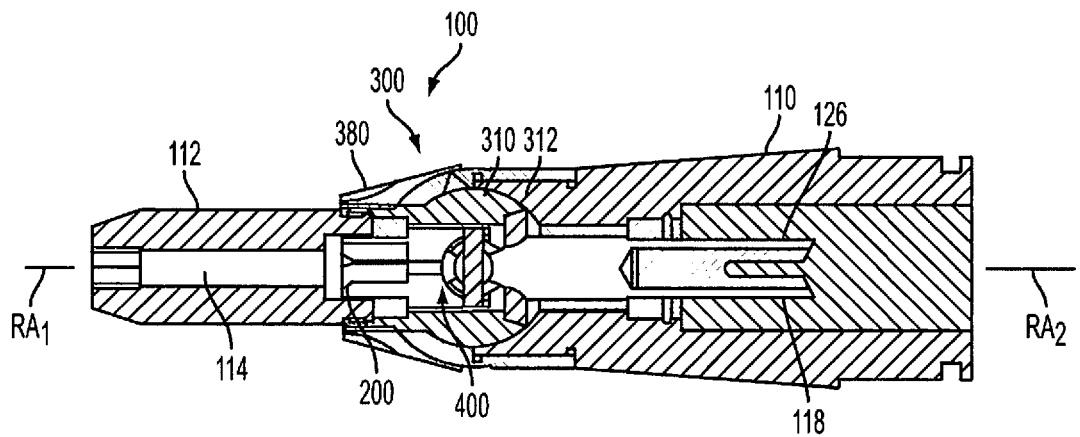
Figure 10:
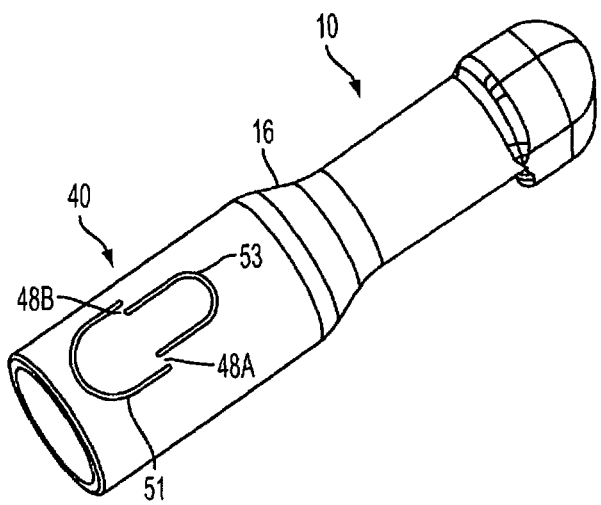
FIG. 10 is a perspective view of a prophy angle with latching mechanism, in accordance with the inventive arrangements.
Figure 11:
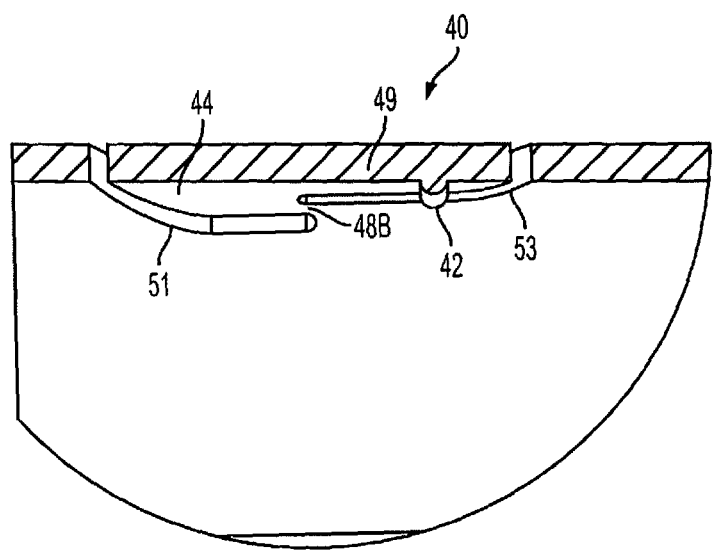
FIG. 11 is a side cross-sectional view of the latching mechanism.

Referring to FIGS. 9A and 9B, an adapter 100 with an outer joint 300 is illustrated. It is noted that although the current illustrated adapter 100 includes a single joint, multiple joints can be provided. Here an adapter 100 can be adjusted from a configuration in which the nose 112 and body 110 share a common centerline (also referred to as a straight adapter, see FIG. 9B) to a configuration in which the centerlines of the nose 112 and the body are at a non-zero degree angle to one another (also referred to as a contra-style or angled adapter, see FIG. 9A). As illustrated in FIGS. 9A and 9B, the ball receiver 312 is positioned on the body 110, and the ball portion 310 is positioned on the nose 112. However, in a different embodiment, in one aspect of the outer joint, the ball-shaped portion can be positioned on the body and the ball receiver can be positioned on the nose. This embodiment of the outer joint 300 can also include a stop that defines a maximum angle that the body 110 can pivot relative to the nose 112. The adapter 100 also includes a shaft 118, which is adjustably connected to a nose rotating member, such as a collet 200, for receiving a prophy rotating member of the prophy angle. The nose 112 includes a first bore 114 for receiving the prophy rotating member and, in certain configurations, a portion of the shaft 118 and/or collet 200. In certain aspects, the adapter 100 includes a multi-axis rotation joint 400 that connects the shaft 118 to the nose rotating member (e.g., collet 200). The multi-axis rotation joint 400 allows for the angle between the rotational axis $RA_2$ of the shaft 118 and the rotational axis $RA_1$ of the collet 200 to be varied. Thus, use of the multi-axis rotation joint 400 permits the adjustable angle adapter 100 to be adjusted while the shaft 118 and collet 200 are rotating. To further enable the adjustable angle adapter 100 to be adjusted during the rotation of the shaft 118 and collet 200, the nose 112 pivots relative to the body 100 about a point that is congruent with the intersection point between the rotational axes $RA_1$, $RA_2$ of the collet 200 and shaft 118. Additionally, the adapter 100 includes an outer joint 300 that connects the body 110 to the nose 112.

In certain configurations, the outer joint 300 permits the nose 112 to pivot relative to the body 110 (or the body 110 to pivot relative to the nose 112). Specifically, the outer joint 300 can permit the nose 112 to pivot relative to the body 110 by at least 18 degrees. Additionally, the outer joint 300 permits the nose 112 to pivot related to the body 110 to multiple different angles between a straight configuration (i.e., 0 degrees) and a maximum-angle configuration (e.g. 18 degrees). In this manner, the adjustable angle adapter 100 provides greater flexibility to a user of the adapter 100. Advantageously, this flexibility can reduce the number of different types of adapters 100 a particular user may require. In certain aspects, the maximum-angle configuration can be as high as 30 degrees. As referred to herein, the pivoting is about a pivot point at the intersection of a centerline of the body 110 and a centerline of the nose 112. The centerline of the body 110 and the centerline of the nose 112 substantially correspond, respectively, to a rotational axis $RA_2$ of the shaft 118 and the rotational axis $RA_1$ of the nose rotating member (e.g., collet 200). As referred to herein, "to pivot" is defined as a change in the angle between the rotational axis $RA_2$ (or centerline of the body 110) of the shaft 118 and the rotational axis $RA_1$ (or centerline of the nose 112) of the nose rotating member (e.g., collet 200). In addition, the outer joint 300 can also permit the nose 112 to rotate relative to the body (or the body 110 to rotate relative to the nose 112.) As the term is used herein, the rotation of the nose 112 and/or body 110 refers to the rotation of the nose 112 and/or body 110 about its own centerline/pivot axis. Additionally, the outer joint 300 can permit the nose 112 to both rotate and pivot relative to the body (or the body 110 rotate relative to the nose 112).

Further, as there are different drive sources with different configurations for coupling with a rotating member, such as the shaft 118. In this regard, in one embodiment, the adapter 100 includes a coupler 126, which is an E-type coupler. In addition, a guard 380 can be provided that creates a seal between the nose 112 and the ball receiver 312. Although not limited in this manner, the engagement of the guard 380 and the ball receiver 312 can act to define a maximum angle that the body 110 can pivot relative to the nose 112.

It is noted the outer portion of the nose 112 may be shaped to mate with the prophy angle. As is known in the art, many types of different types of prophy angles exist that have different mating profiles, and the present adapter 100 is not limited as to a particular shape of the nose 112 and as to a particular profile of prophy angle with which the nose 112 can mate. However, in a certain aspects of the adapter 100, the nose 112 is configured as a doriot-style adapter. Depending upon the type of prophy angle, other types of connections devices include, but are not limited to, latch type, 3-ball chuck, attachment ring, push chuck, quick-connect collars, autochucks, E-type (i.e., ISO 3964), DIN 13940, ISO 1797, U-type, NSK type, and Midwest.

Now referring to FIGS. 10, 11, and 12A-12D, a prophy angle 10 with a latching mechanism 40 is illustrated. The latching mechanism 40 includes a latch element 49, a male/female latch protrusion 42, and a lever 44 that engages and/or disengages the male/female latch protrusion 42. The nose 112 of the adapter also includes a female/male element 46 that is configured to engage the male/female protrusion 42 of the latching mechanism 40 in the prophy angle 10. Although the latching mechanism 40 is illustrated with a shaft-less prophy angle 10, the latching mechanism 40 may also be employed with a prophy angle having a prophy rotating member (i.e., shaft).

Although the latch protrusion 42 is illustrated as a male element and element 46 of the nose 112 as a female element, these configurations can be swapped. In operation, referring to FIG. 12B, as the prophy angle 10 is placed over the nose 112, the nose 112 displaces the latch element 49 and, thus, the latch protrusion 42 from its resting orientation relative to the remainder of the prophy angle 10. However, referring to FIG. 12C, as the prophy angle 10 is fully inserted onto the nose 112, the latch protrusion 42 is released from its displaced orientation and is positioned within the female element 46 (e.g., a groove) in the nose 112. In so doing, the latch protrusion 42 prevents removal of the prophy rotating member from collet.

Figure 12A:
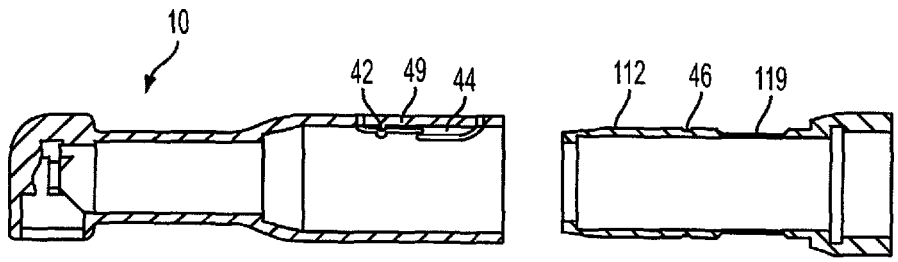
FIGS. 12A-12D are, respectively, cross-sectional view of the prophy angle with latching mechanism and nose of the adapter in a disassembled, partially-assembled, fully-assembled and latched, and full-assembled and unlatched configurations.
Figure 12B:
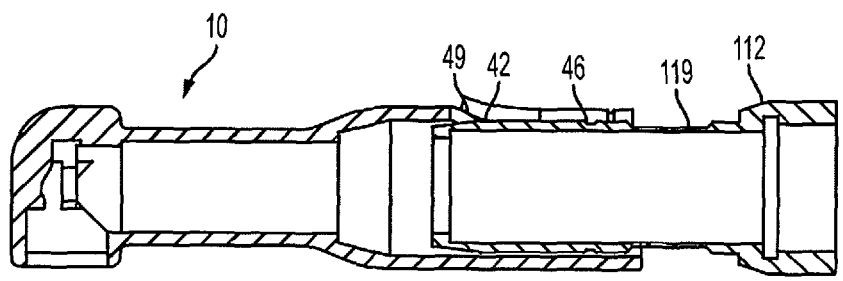
Figure 12C:
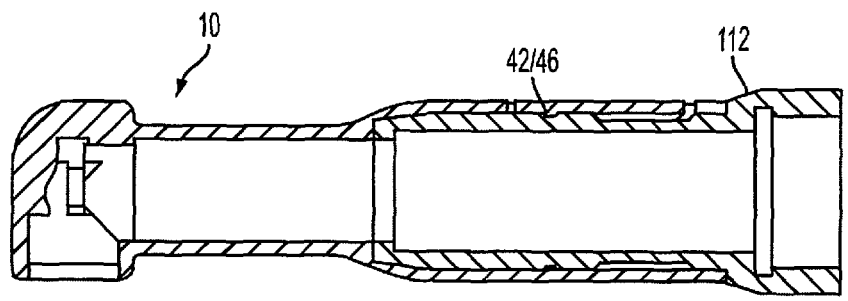
Figure 12D:
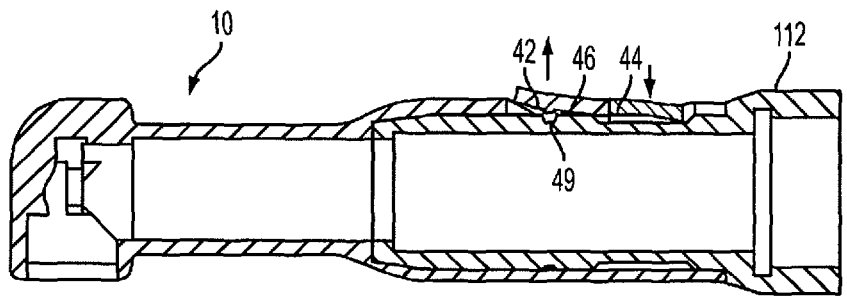

Referring to FIG. 12D, to release the latching mechanism, the lever 44 is depressed (see down arrow), which acts to rotate the latch element 49 and the latch protrusion 42 about a pair of pivots 48A, 48B (as labeled in FIG. 10) and out of the groove 46 in the nose 112 (see up arrow). To permit depressing of the lever 44, a depression 119 (as labeled in FIG. 12A, 12B) is formed in the outer surface of the nose 112 proximate the groove 46. Thus, as illustrated, movement of the lever 44 between a first position (not depressed) (e.g., FIG. 12C) and a second position (depressed) (e.g., FIG.

12D) moves the latch protrusion 42 between an engaged position and a disengaged position.

Referring again to FIG. 10, although not limited to this particular configuration, each one of the pair of pivots 48A, 48B is defined by a pair of substantially parallel and opposing slots 51, 53 within the housing. Also, a first one 51 of the pair of slots of the first pivot 48A connects to a first one 51 of the pair of slots of the second pivot 48B, and a second one 53 of the pair of slots of the first pivot 48A connects to a second one 53 of the pair of slots of the second pivot 48B. The latch mechanism 40 may be formed from the housing 16 of the prophy angle 16. Although not limited to this particular configuration, the lever action of the latch mechanism 40 may be formed by including a pair of opposing U-shaped slots 51, 53 within the housing 16. Additionally, the latch protrusion 42 may be disposed within the bounds of the U-shaped slot within the housing 16. As can be readily envisaged, the slots 51, 53 are not limited to a U-shape. For example, one or both of the slots 51, 53 could be V-shaped, rectangular-shaped, or shaped like a half moon.

Figure 13A:
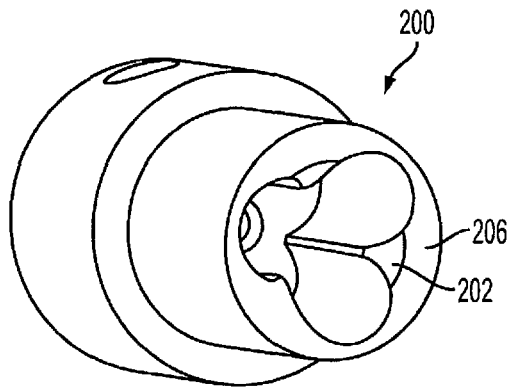
FIGS. 13A-13C are, respectively, a front perspective view, a front plan view, and a side cross-sectional view of a collet in accordance with the inventive arrangements.
Figure 13B:
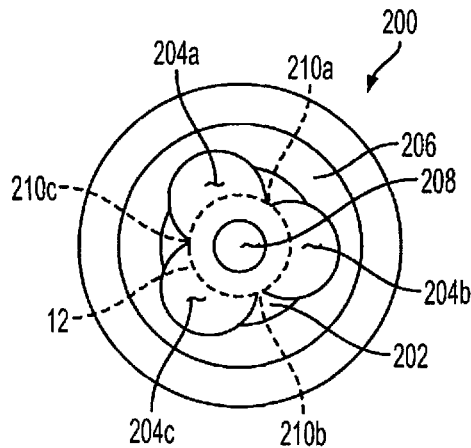
Figure 13C:
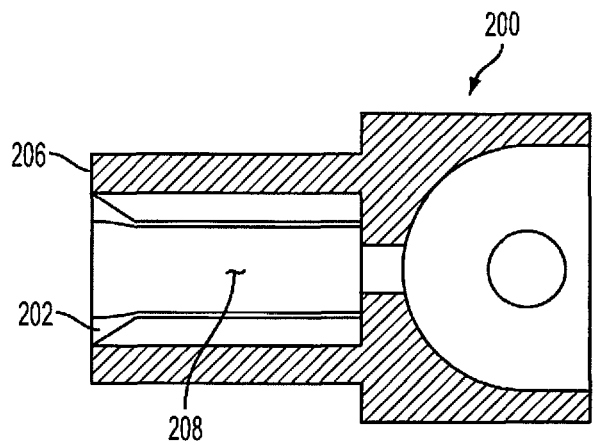

FIGS. 13A-13C further illustrate the collet 200. The collet 200 of the adapter is adapted to receive and hold the prophy rotating member 12 of the prophy angle 10. In certain aspects of the adapter, the collet 200 is not limited in the manner in which the collet 200 receives and holds the prophy rotating member 12, and any configuration of the collet 200 so capable is acceptable for use with the adapter. In certain aspects of the adapter, the collet 200 includes a plurality of extensions 210a-210c for receiving the prophy rotating member 12 (see FIG. 13B). The innermost portions of the extensions 210a-210c define an inner collet bore 208 having a diameter slightly less than the diameter of the prophy rotating member 12. In this manner, upon the prophy rotating member 12 being positioned within the inner collet bore 208, an interference fit or friction grip exists between the plurality of extensions 210a-210c and the prophy rotating member 12. The interference fit allows the extensions 210a-210c to hold onto the prophy rotating member 12 and to transfer rotation from the collet 200 to the prophy rotating member 12. In certain aspects of the collet 200, the innermost portions of the extensions 210a-210c define an inner collet bore 208 having a fixed diameter.

As further illustrated in FIGS. 13A-13C, the outer edge of each extension 210a-210c may also include a concave surface. The concave surfaces of the extensions 210a-210c can define the outer circumference of the inner collet bore 208 of the collet 200. These concave surfaces also mate with the outer surface of the prophy rotating member 12 to form the interference fit between the plurality of extensions 210a-210c and the prophy rotating member 12. Although not limited in this manner, the radius of the concave surfaces of the extensions 210a-210c is substantially equal to the radius of the collet bore 208. Although not limited in this manner, in certain aspects of the collet 200, the concave surfaces define less than 20% of the circumference of the collet bore 208.

Further, the collet 200 may also include longitudinal chamfers 202 on the extensions 210a-210c. The chamfers may extend from a collet distal end 206 along each extension 210a-210c and slope inwardly towards the rotational axis of the collet 200. The longitudinal chamfers 202 provide a guide for receiving the prophy rotating member 12. As the prophy rotating member 12 is moved into the collet 200, the longitudinal chamfers 202 guide the prophy rotating member 12 toward the inner collet bore 208. Although not limited in this manner, a face of the longitudinal chamfers 202 may be angled at about 60°±15° relative to the face of the distal end 206 of the collet 200.

The manner in which the inner collet bore 208 is formed is not limited. For example, the inner collet bore 208 may be formed by drilling the collet 200 along its centerline. By forming the inner collet bore 208 in this manner, the concave surfaces at the outer edge of each extension 210a-210c may also be formed. Also, the extensions 210a-210c may be formed by drilling offset bores 204a-204c, which have a centerline offset from the centerline of the collet 200. Although the term "drilling" is used herein, other methodology used to form bores/holes is also acceptable.

Many types of joints are capable of transferring rotation from a first rotating member to a second rotating member, which is positioned off-axis from the first rotating member, and the present adjustable angle adapter is not limited as to a particular type of joint so capable. In a current aspect of the adapter, the multi-axis rotation joint is a yoke and joint, as illustrated in FIGS. 14A-14C and 15A-15B.

Figure 14B:
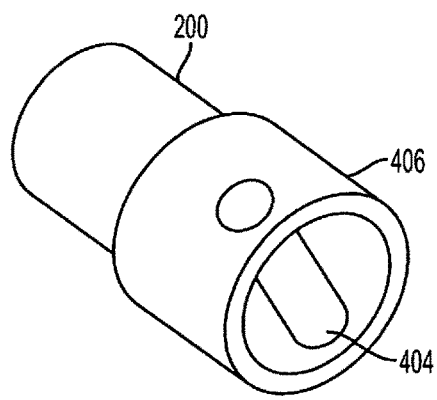

Referring to FIGS. 14A-14C and 15A-15B, elements of a multi-axis rotation joint are illustrated. In FIGS. 14A and 14B, the collet 200 is connected to a receiver 406 for receiving a head of the multi-axis rotation joint. Although shown connected to the collet 200, the receiver 406 may be integral with the collet 200. Alternatively, another member (not shown) may be positioned between the receiver 406 and the collet 200. The use of a multi-axis rotation joint advantageously reduces back lash, which is inherent in many types of joints. The receiver 406 includes openings 408 into which a second pin 404 is positioned. Although the second pin 404 may rotate within the openings 408 of the receiver 406, in a current aspect of the multi-axis rotation joint, the second pin 404 is positionally and rotationally fixed relative to the receiver 406. In so doing, the second pin 404 is prevented from moving within the receiver 406. Since the receiver 406, and thus the ends of the second pin 404, can rotate about the rotational axis of the collet 200 at very high speeds, any movement of the ends of the second pin 404 beyond the outer circumference of the receiver 406 may cause engagement between the ends of the second pin 404 and inner surfaces of the nose and/or the body of the adapter. This engagement may cause failure of or damage to the adapter and/or the multi-axis rotation joint.

The manner in which the second pin 404 is prevented from moving within the receiver 406 is not limited as to a particular technique or arrangement. For example, the second pin 404 can be attached to the receiver, for example, via welding or gluing. However, in a current aspect of the multi-axis rotation joint, the second pin 404 is sized slightly greater than the size of the openings 408 of the receiver 406 such that upon inserting the second pin 404 into openings 408, an interference fit exists between the second pin 404 and the openings 408.

Figure 14C:
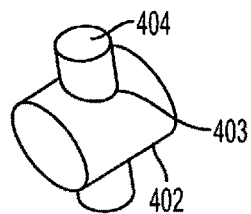
Figure 14D:
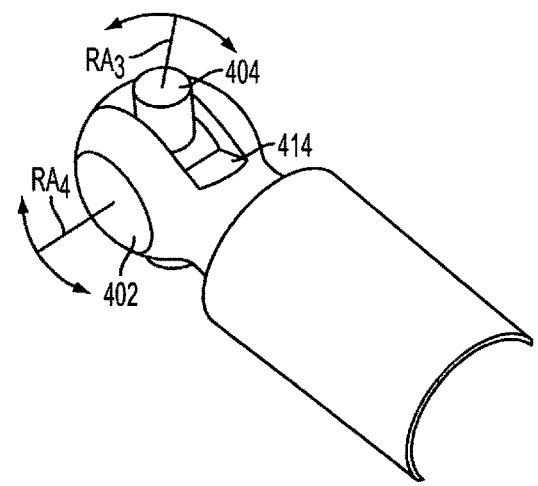
Figure 15A:
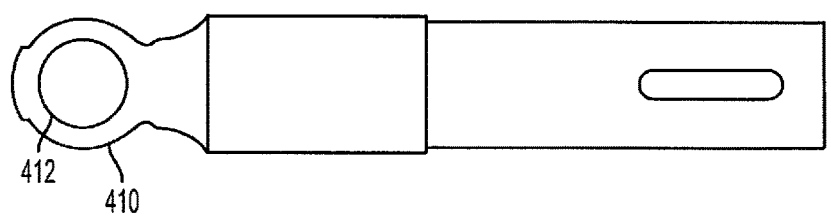
FIGS. 15A and 15B are, respectively, side and top views of the head of the multi-axis rotation joint and a shaft to which the head is connected.
Figure 15B:
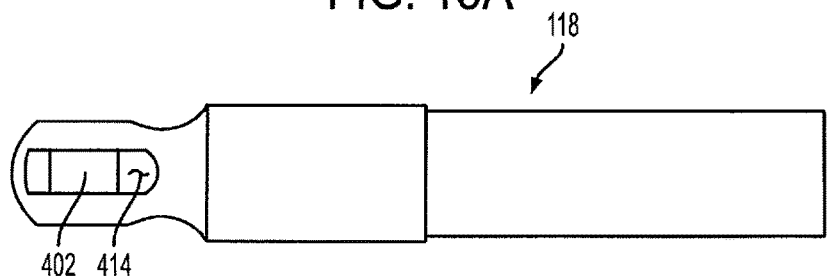

Referring now to FIGS. 14C and 14D, the second pin 404 is positioned within an opening 403 of a first pin 402, and the first pin 402 is positioned within a head. Further in FIG. 14D and in FIGS. 15A and 15B, the head 410 includes slots 414 through which the second pin 404 extends. As presently configured, the first pin 402 rotates within and relative to the head bore 412 of the head 410 about a rotational axis $RA_4$, and the second pin 404 rotates within relative to the first pin 402 about a rotational axis $RA_3$. The outside diameter of the second pin 404 is somewhat less than the inside diameter of the inside diameter of the opening 403 of the first pin 402 to form a close tolerance slip fit between the second pin 404 and the first pin 402. Similar, the outside diameter of the first pin 402 is somewhat less than the inside diameter of the head bore 412 of the head 410 to form a close tolerance slip fit between the first pin 402 and the head bore 412 of the head 410.

Although not limited as to a particular range of rotation or to the particular manner described herein, the first pin 402, while within the head 410, is limited in its range of rotation by the length of the slot 414 in the head 410. As the length of the slot 414 increases, the range of the rotation of the first pin 402 within the head 410 is also increased. Conversely, upon the length of the slot 414 decreasing, the range of rotation of the first pin 402 within the head 410 is also decreased. The width of the slots 414 may be slightly less than the outside diameter of the second pin 404 to allow the second pin 404 to move from side-to-side within the slots 414.

With regard to the range of rotation of the second pin 404 within the first pin 402, the range of rotation is not necessarily limited when the first pin 402 is within the second pin 404 alone. However, upon the joint being fully assembled, the range of rotation of the second pin 404 within the first pin 402 may be limited to some degree by interference between the collet 200 and the shaft 118. Although illustrated as the head 410 being connected to the shaft 118 and the receiver 406 being connected to the collet 200, the multi-axis rotation joint is not limited in this manner. For example, the head 410 may be connected to the collet 200, and the receiver 406 may be connected to the shaft 118.

Figure 16:
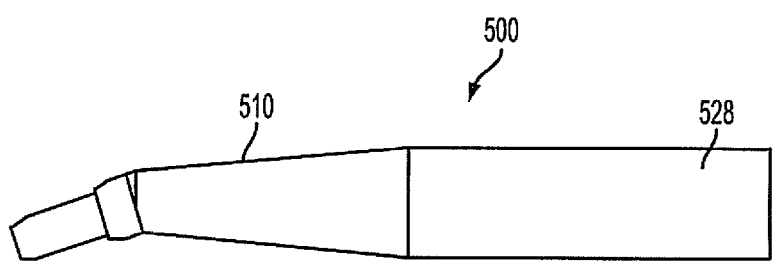
FIG. 16 is a side view of an adapter with an integral micromotor.
Figure 17:
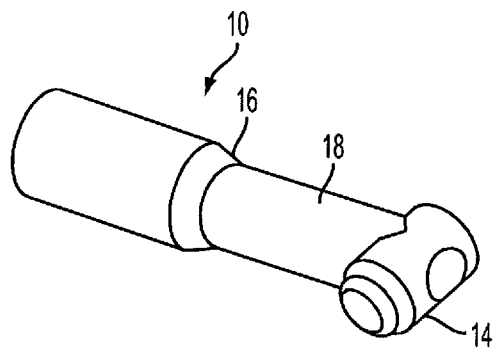
FIG. 17 is a perspective view of a prophy angle according to the prior art.
Figure 18:
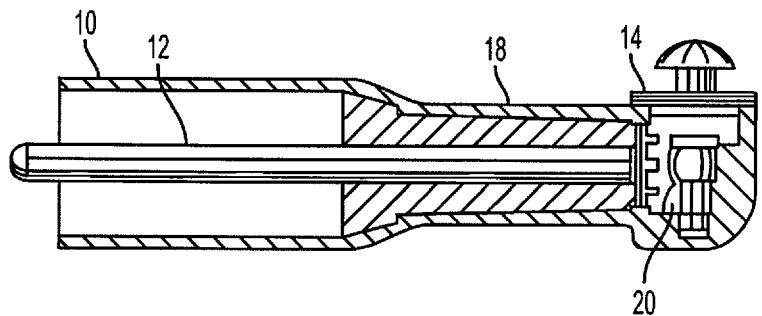
FIG. 18 is a side cross-sectional view of the prophy angle according to the prior art.

FIG. 16 illustrates an adjustable angle adapter 500 with an micromotor 528 that is integral with the body 510 of the adjustable angle adapter 500. Upon using an integral micromotor 528 with the adjustable angle adapter 500, the shaft may be directly connected to both the micromotor 528 and joint. Using micromotors to drive dental equipment is well known by those in the art, and any micromotor 528 so capable is acceptable for use with the adjustable angle adapter 500. Examples of micromotors 528 include electrically-driven and pneumatically-driven motors. In the presently-illustrated adjustable angle adapter, the micromotor 528 is pneumatically driven.

Referring to FIGS. 19A and 19B, a shaft-less prophy angle 10SL and an adapter 100 with an integrated drive shaft 350 is illustrated. With shaft-less prophy angles 10SL, the shaft is an integral part of the nose 112. Although illustrated with a non-adjustable adapter 100, these concepts are also applicable to an adjustable adapter. The adapter 100, directly or indirectly, provides the rotational movement to a gearing system of a rotor 20 of the prophy angle 10. The adapter 100 includes a body 110 and a nose 112. The adapter 100 includes a shaft 118 that is connected to a drive shaft 350 via a coupler 400.

The shaft 118 is rotated by the drive source 450. As is known in the art, many different types of drive sources 450 exist and these different drive sources 450 have different configurations for coupling with a rotating member, such as the shaft 118. In this regard, the present adapter 100 is not limited as to drive source 450 for the adapter 100. For example, the drive source 450 may be connectable to the adapter 100. Alternatively, the drive source 450 may be integrated with the adapter 100. Also, examples of drive sources 450 include electrically-driven and pneumatically-driven motors In addition, the drive shaft 350 is a part of the adapter 100. In other aspects, the drive shaft 350 is removably attachable to a collet within the adapter 100. In so doing, the drive shaft 350 can be replaceable and/or cleaned. A slideable sleeve 460 may be positioned over the drive shaft 350. The slideable sleeve 460 moves from an extended position (FIG. 19A), which conceals the gear 352 of the drive shaft 350, to an retracted position (FIG. 19B), which reveals the gear of the drive shaft 350. The slideable sleeve 460 is not limited in the manner in which the slideable sleeve 460 moves from the extended position to the retracted position and back again. The gear 352 is configured to engage the prophy angle 10 to drive rotor 20.

The invention claimed is:

1. A dental system comprising a dental prophy angle received by an adapter, wherein the dental prophy angle comprises:
a housing;
a rotor disposed within a distal end of the housing;
a guard comprising an inner surface that is concave, the guard extending from a receiving end of the housing, wherein
the guard has a greatest outer diameter larger than a greatest outer diameter of the housing;
the adapter comprising a nose, a monolithic ball portion having an integral neck, and a ball receiver comprising a distal portion with a convex outer surface and a concave inner surface and a proximal portion extending away from the nose, the nose coupled to the integral neck of the monolithic ball portion, wherein
the housing comprising a configuration to receive the nose of the adapter,
the concave inner surface of the ball receiver engages a convex outer surface of the monolithic ball portion,
the concave inner surface of the guard engages the convex outer surface of the ball receiver, and
the integral neck extending from the monolithic ball portion toward the rotor.

2. The dental system of claim 1, wherein the greatest outer diameter of the guard is at least 10% larger than the greatest outer diameter of the housing.

3. The dental system of claim 1, wherein the greatest outer diameter of the guard is at least 20% larger than the greatest outer diameter of the housing.

4. The dental system of claim 1, wherein the concave inner surface of the guard includes a plurality of inwardly-extending ribs.

5. The dental system of claim 4, wherein the plurality of ribs radially extend from a center of the guard.

6. The dental system of claim 1, wherein the concave inner surface of the guard includes a radius that substantially matches a radius of the convex outer surface of the ball receiver of the adapter.

7. The dental system of claim 6, wherein the concave inner surface of the guard is configured to form a seal between the concave inner surface of the guard and the convex outer surface of the ball receiver.

8. The dental system of claim 1, wherein the greatest outer diameter of the guard is at an end of the guard closest to the ball receiver and wherein at an opposite end of the guard, the guard has a smaller diameter than both a diameter measured at a midpoint of the guard and also the greatest outer diameter at the end of the guard closest to the ball receiver.

9. The dental system of claim 1, wherein an end of the guard distal to the ball receiver both rests on an outer curved surface of a neck of the nose and also overlaps the neck of the nose.

10. The dental system of claim 1, wherein the guard tapers from the greatest outer diameter of the guard being at an end of the guard closest to the ball receiver to an opposite end of the guard having a diameter less than the greatest outer diameter.

\* \* \* \* \*